(12) United States Patent
Garrido Garza et al.

(10) Patent No.: US 10,379,023 B2
(45) Date of Patent: Aug. 13, 2019

(54) DIGITAL HYDROMETER ASSISTANT READER

(71) Applicant: Fresenius Medical Care Holdings, Inc., Waltham, MA (US)

(72) Inventors: Hernando Garrido Garza, Concord, CA (US); Philip James, Orinda, CA (US); Gilberto Romero Saldivar, Barcelona (ES); Matin Vareth, Clayton, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 99 days.

(21) Appl. No.: 15/351,836

(22) Filed: Nov. 15, 2016

(65) Prior Publication Data

US 2018/0136102 A1 May 17, 2018

(51) Int. Cl.
*G01N 9/18* (2006.01)
*G01N 9/14* (2006.01)

(52) U.S. Cl.
CPC .............. *G01N 9/18* (2013.01); *G01N 9/14* (2013.01)

(58) Field of Classification Search
CPC .. G01N 9/18; G01N 9/10; G01N 9/12; G01N 9/14; G01N 9/16
USPC ........... 73/444–454, 313; 340/603, 612, 623, 340/624
See application file for complete search history.

(56) References Cited

U.S. PATENT DOCUMENTS

| 2,267,115 | A |   | 12/1941 | Linebarger |          |
|-----------|---|---|---------|------------|----------|
| 2,273,850 | A |   | 2/1942  | Ewald      |          |
| 2,362,661 | A |   | 11/1944 | Peters et al. |       |
| RE24,075  | E | * | 10/1955 | Giers      | G01N 9/16 |
|           |   |   |         |            | 73/304 C |
| 3,126,745 | A | * | 3/1964  | Lutke      | G01N 9/22 |
|           |   |   |         |            | 73/453   |
| 3,921,461 | A |   | 11/1975 | Layton     |          |

(Continued)

FOREIGN PATENT DOCUMENTS

| DE | 3631884 A1 | 3/1988 |
| DE | 3632019 A1 | 3/1988 |

(Continued)

OTHER PUBLICATIONS

International Search Report (Form PCT/ISA/210) for International Patent Application No. PCT/US2017/057358, issued from the European Patent Office, dated Jan. 23, 2018, 5 pages.

(Continued)

*Primary Examiner* — Robert R Raevis
(74) *Attorney, Agent, or Firm* — Kilyk & Bowersox, P.L.L.C.

(57) ABSTRACT

A digital hydrometer and methods of digitally displaying a specific gravity measured by a hydrometer are provided. The digital hydrometer can comprise a base, a displacement vessel, an inductive distance sensor, an output circuit, and a hydrometer float. The displacement vessel and inductive distance sensor can be mounted in or on the base. The displacement vessel can hold a displacement fluid. The hydrometer float can float in the displacement fluid. The output circuit can be in electrical communication with the inductive distance sensor and comprise a digital display device configured to display a digital value that is commensurate with a change in impedance attributable to the proximity of a metallic object, in the hydrometer float, to the (Continued)

sensor or its inductor. The digital value can be a specific gravity of the displacement fluid.

11 Claims, 10 Drawing Sheets

(56) References Cited

U.S. PATENT DOCUMENTS

| | | | |
|---|---|---|---|
| 3,964,317 | A | 6/1976 | Blanchard |
| 4,030,027 | A | 6/1977 | Yamada et al. |
| 4,160,204 | A | 7/1979 | Holmgren et al. |
| 4,400,978 | A | 8/1983 | Guay et al. |
| 4,557,186 | A | 12/1985 | Brown |
| 4,956,606 | A | 9/1990 | Kwiatkowski et al. |
| 5,066,912 | A | 11/1991 | Kwiatkowski |
| 5,587,527 | A | 12/1996 | Radford et al. |
| 5,830,375 | A | 11/1998 | Huang et al. |
| 5,900,547 | A * | 5/1999 | Bartkiewicz ............ G01N 9/18 73/32 R |
| 6,192,753 | B1 | 2/2001 | Czarnek |
| 6,218,949 | B1 * | 4/2001 | Issachar ................. G01F 23/62 340/603 |
| 6,418,788 | B2 | 7/2002 | Articolo |
| 9,026,395 | B2 | 5/2015 | Beaulieu et al. |
| 2014/0157992 | A1 | 6/2014 | Farotto |

FOREIGN PATENT DOCUMENTS

| | | | |
|---|---|---|---|
| GB | 761880 | A | 11/1956 |
| GB | 793630 | * | 4/1958 |
| GB | 865505 | * | 4/1961 |
| GB | 2250597 | A | 6/1992 |

OTHER PUBLICATIONS

Written Opinion of the International Searching Authority (Form PCT/ISA/237) for International Patent Application No. PCT/US2017/057358, issued from the European Patent Office, dated Jan. 23, 2018, 7 pages.

Tomek, J., "Inductive Contactless Distance Measurement Intended for a Gastric Electrical Implant," Acta Polytechnica vol. 47, No. 4-5/2007, pp. 76-79, Czech Technical University Publishing House.

"Precision Transimpedance Logarithmic Amplifier with Over 5 Decades of Dynamic Range," MAX4206, Maxim Integrated Products, Inc., 19-3071; Rev 2; May 2015, pp. 1-17.

"Precision Logarithmic and Log Ratio Amplifier," SBOS242B—May 2002—Revised Jun. 2004, Burr-Brown Products from Texas Instruments, Texas Instruments Incorporated, Dallas, Texas, pp. 1-17.

* cited by examiner

DIGITAL HYDROMETER ASSISTANT READER

BACKGROUND OF THE INVENTION

The present invention relates to a digital hydrometer and methods of digitally displaying a specific gravity measured by a hydrometer.

A hydrometer is an instrument used to measure the specific gravity (or relative density) of liquids; that is, the ratio of the density of the liquid to the density of water. A traditional hydrometer is usually made of glass and consists of a cylindrical stem and a bulb weighted with mercury or lead shot to make it float upright. These analog hydrometers are typically very hard to read, because the numbers and scales on these instruments are very small and closely spaced.

Traditional hydrometers are currently used by hemodialysis clinics to measure the specific gravity of acid concentrate when a batch of dry acid concentrate is prepared at a clinic. The patient care technician or nurse that prepares the batch of dry acid concentrate has to verify that the specific gravity reading given by the hydrometer is within pre-determined acceptance criteria in order to accept or reject a batch. Therefore, it is critical to the process that the hydrometer readings are taken correctly, accurately, and precisely.

Accordingly, there exists a need for a hydrometer that allows for more accurate and precise measurements of specific gravity, in particular, for measuring the specific gravity of a dialysate, acid concentrate batch.

SUMMARY OF THE PRESENT INVENTION

A feature of the present invention is to provide a more accurate and precise device and method for reading a hydrometer float to determine a specific gravity of the liquid in which it floats.

Another feature of the present invention is to provide a device and method for digitally displaying a specific gravity measured and calculated from a hydrometer reading.

A further feature of the present invention is to provide a device and method for calibrating a specific gravity measurement.

An additional feature of the present invention is to provide a device and method for determining whether or not an acid concentrate batch is acceptable for use in a dialysis machine based on the specific gravity, or parameter correlated therewith, of the acid concentrate batch.

Additional features and advantages of the present invention will be set-forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a digital hydrometer comprising a base, a displacement vessel, an inductive distance sensor, an output circuit, and a hydrometer float. The base can have a top surface. The displacement vessel can be mounted in or on the base and extend upwardly from the top surface. The inductive distance sensor can be mounted in or on the base. The inductive distance sensor can have any relevant circuitry, for example, an inductor that provides an impedance that varies in relation to a proximity of a metal object in the displacement vessel. The output circuit can be in electrical communication with the inductive distance sensor and comprise a digital display device configured to display a digital value that is commensurate with a change in impedance attributable to the proximity of a metallic object to the inductor. A hydrometer float can have a top end and a bottom end and can be sized and configured to float in a displacement fluid in the displacement vessel. The hydrometer float can also comprise a metallic object that changes the impedance of the inductor. The metallic object can be positioned at, on, or at a fixed distance from, the bottom end of the hydrometer float. The metallic object can affect a change in impedance varying in relation to the proximity of the metallic object to the inductor. The output circuit can be configured to generate a signal based on the change of impedance caused by the metallic object. The output circuit can convert the signal into a digital value to be displayed by the digital display device.

The present invention further relates to method of calculating a specific gravity of a test liquid. The method can be performed using a digital hydrometer of the present invention. For example, a method of calculating a specific gravity of a test liquid can include the following steps. A first measured amount of the test liquid can be placed in a displacement vessel. The top of the liquid can define a liquid surface. A hydrometer float can be floated in the test liquid in the displacement vessel. The hydrometer float can comprise a metallic object configured to change the impedance produced by an inductor, for example, of an inductive distance sensor, by an amount that varies based on the proximity of the metallic object to the inductor. The hydrometer float can comprise a top end and a bottom end. The hydrometer float can have a buoyancy that causes the top end to extend above the liquid surface and the bottom end to be submerged in the test liquid below the liquid surface. An impedance caused by the proximity of the metallic object to the inductor can be measured. The specific gravity of the liquid can be calculated by converting the impedance to a corresponding specific gravity value, which can be displayed digitally.

It is to be understood that both the foregoing general description and the following detailed description are exemplary and explanatory only and intended to provide a further explanation of the present invention, as claimed.

DETAILED DESCRIPTION OF THE PRESENT INVENTION

Figure 1:
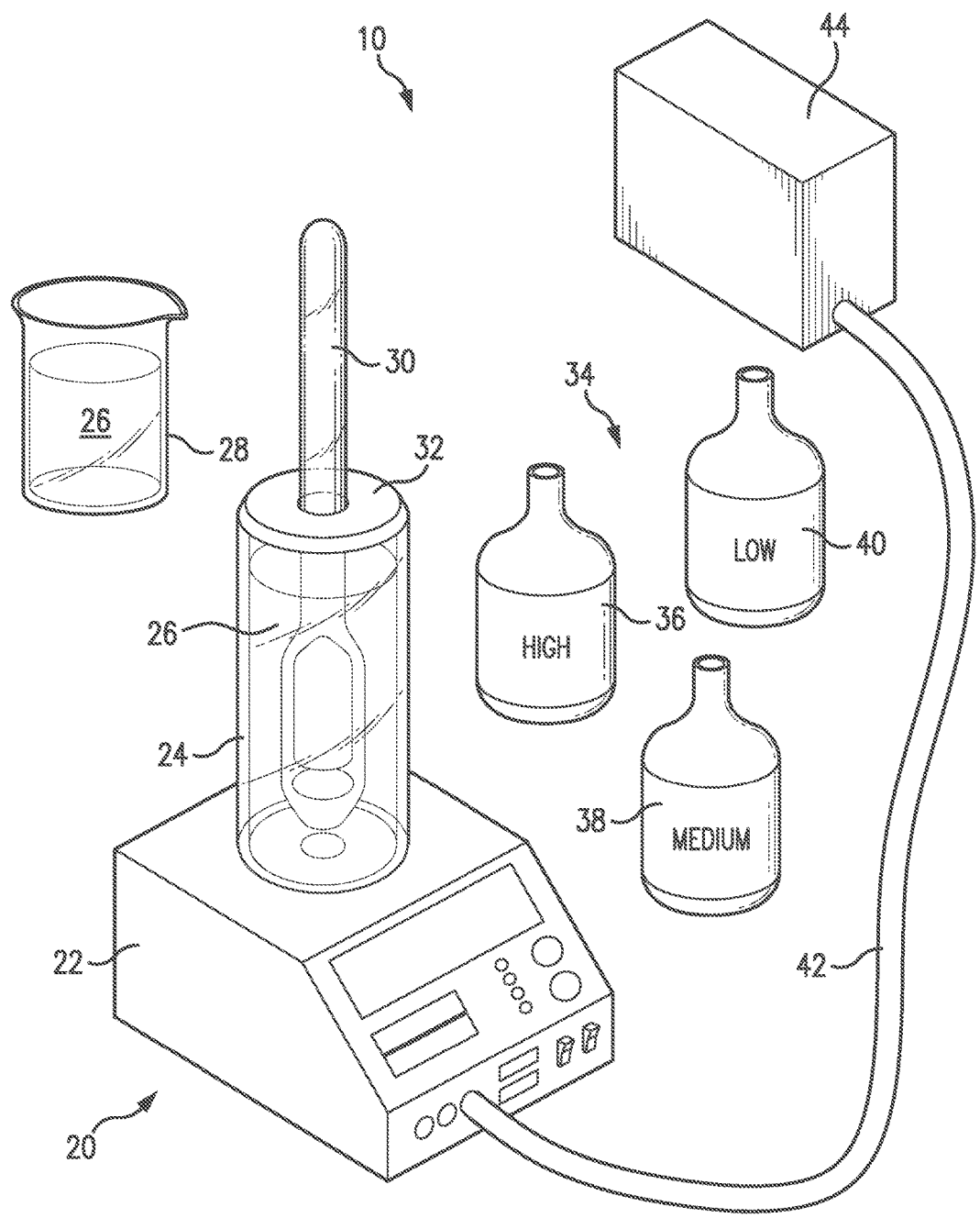
FIG. 1 is a perspective view of a system including a digital hydrometer and related components, in accordance with the present invention.

The present invention relates to a digital hydrometer comprising a base, a displacement vessel, an inductive distance sensor, an output circuit, and a hydrometer float. The base can have a top surface. The displacement vessel can be mounted in or on the base and extend upwardly from the top surface. The top surface can lie in a single plane or can have raised and/or recessed portions configured to center or otherwise help maintain a desired position of the displacement vessel. The inductive distance sensor can be mounted in or on the base. The sensor can be housed completely in the base or can extend upwardly from the base. If the sensor extends upwardly from, or is mounted on, the exterior of the base, the displacement vessel can be provided with a vessel bottom having a dome, cavity, or similar concave shape to mate with the sensor. The inductive distance sensor can have any relevant circuitry, for example, an inductor that provides an impedance that varies in relation to a proximity of a metal or metallic object in the displacement vessel.

The output circuit can be in electrical communication with the inductive distance sensor and comprise a digital display device configured to display a digital value that is commensurate with a distance measured, for example, calculated by measuring a change in impedance attributable to the proximity of the inductor to a metallic object in or on the hydrometer float. The hydrometer float can have a top end and a bottom end that is sized and configured to float in a displacement fluid in the displacement vessel. The hydrometer float can comprise a metallic object that changes the impedance generated by the inductor. The metallic object can be positioned at, on, or at a fixed distance from, the bottom end of the hydrometer float. The metallic object can affect a change in impedance that varies in relation to the proximity of the metallic object to the inductor. The output circuit can be configured to generate a signal based on the change of impedance caused by the metallic object. The output circuit can convert the signal into a digital value to be displayed by the digital display device.

Any suitable inductive distance (proximity) sensor, induction circuit, and/or inductor can be used. For example, the inductor can be a single coil inductor. The induction circuit can comprise a high frequency signal source and an electronic bridge connected to the high frequency signal source, the electronic bridge comprising a plurality of branches including a first branch that comprises the inductor. For example, the high frequency signal source can comprise an oscillator, the inductor can comprise a single coil inductor, and the plurality of branches can further comprise a second branch, a third branch, and a fourth branch, each of which provides a fixed, known impedance.

The digital hydrometer base can comprise a base housing and the output circuit can be contained in or on the base housing. The digital display device can be mounted on the base housing or be provided as an external device. Any number or type of displays can be included either as part of the digital hydrometer, part of an external device, or both. The digital display can include a seven-digit display, an LCD display, an LED display, a numerical display, a threshold display, a bulb, an LED, a color indicator, or a combination thereof. The display can display numbers, text, images, and/or video. The display can be passive or can be interactive, for example, the display can include a touchscreen and be configured as a graphical user interface (GUI). The digital hydrometer base can further comprise one or more data outlets in electrical communication with the output circuit and configured to transmit output data, via a wired or a wireless connection, to an external device. Accordingly, a system is also provided by the present invention, which can comprise the digital hydrometer and the external device, and the external device can be configured to receive output data from the digital hydrometer. The external device can include, for example, a computer, a network, a handheld device, a mixer, a dialysate concentrate mixing device, a dialysis machine, or a combination thereof. The digital hydrometer can be remote from the external device. The digital hydrometer can be on or housed in an external device, in which case the device can be referred to instead as a parent device, a sister device, a system, a complementary device, a compatible device, or the like. For example, the digital hydrometer can be mounted on or housed in a dialysate mixer or dialysis machine.

The digital hydrometer can include any relevant circuitry associated with, overlapping with, in operative association with, and/or complementing, the induction circuit and the inductive distance sensor. For example, the digital hydrometer can further comprise a calibration circuit in electrical communication with and configured to calibrate the inductive distance sensor. The digital hydrometer can further comprise a processor circuit in digital communication with the inductive distance sensor. The processor circuit can be configured to calculate a specific gravity of a displacement fluid in the displacement vessel based on a signal generated by the output circuit, and to digitally display the calculated specific gravity. The digital hydrometer can further include a memory circuit in digital communication with the processor circuit and can be configured to store the calculated specific gravity. The memory circuit can include any number or type of memories, for example, a random access memory (RAM), a read only memory (ROM), both, or the like. The memory circuit can comprise an internal memory and/or an external memory, for example, a thumb (flash) drive or hard drive in communication with the digital hydrometer.

The output, inductive, calibration, processor, and memory circuits can be configured to work together to measure a change in impedance or other change to calculate a specific gravity. Impedances measured and associated with calibration fluids of known specific gravities can be stored in the memory circuit and be accessed by the processor circuit to determine the specific gravity of a test liquid of unknown specific gravity. The specific gravity determined can be displayed on the digital display. The digital hydrometer can further include a control circuit for controlling these various functionalities. The control circuit can include or be in operative communication with one or more user interfaces, locally, or via an external device, for example, a touch-screen, a keyboard, and/or a mouse. Any connection or communication described herein as electrical can also or instead be optical, for example, fiber optic, laser, or a combination thereof. Electrical connections and communications described herein can comprise both wired and wireless connections and communications, unless otherwise indicated.

The digital hydrometer can include or utilize any suitable hydrometer float. The hydrometer float can be, for example, a traditional (analog) hydrometer that heretofore was read by eye directly from the position of the hydrometer relative to the surface of the liquid being measured for specific gravity. The hydrometer float can be a shaft that includes a bulb and a stem extending upwardly from the bulb. The hydrometer float need not, however, have a bulb and/or a stem, provided that it has sufficient buoyancy to float and a geometry that enables it to move freely vertically within the displacement vessel. The hydrometer float can include a hollow shaft containing a gas and the metallic object can be fixed at a bottom end thereof. The gas can be contained with a chamber of the hydrometer float. The chamber can be in the bulb, the stem, or both. The hydrometer float can further comprise a ballast at or near the bottom end of the float to aid in buoyancy, in conjunction with gas in the chamber. The ballast can comprise or be the metallic object.

The hydrometer float can include one or more metallic objects configured to be sensed remotely by the inductive distance sensor. The metallic object can be housed within the hollow shaft proximal, at, or on the bottom end of the hydrometer float. The metallic object can alternatively or additionally be provided, for example, as a coating, foil, or wound wire, on an exterior surface of the hydrometer float. The metallic object can be or comprise iron, copper, aluminum, silver, gold, platinum, nickel, palladium, molybdenum, tungsten, iridium, titanium, zinc, tin, cobalt, mercury, or a combination thereof. The metallic object can comprise a sheet, a foil, a wire, a wound wire, a coil, a solenoid, a mesh, particles, a spheroid, a nodule, a rod, a tube, a cylinder, a cone, a torus, a hollow body, a solid body, a coating, a dispersion, a suspension, or a combination thereof. The metallic object can comprise a magnetic material, for example, a permanent magnetic material, a ferromagnetic material, a paramagnetic material, an induced magnetic material, or a combination thereof. The metallic object can be provided as a single metallic object or as a group of two or more metallic objects positioned relative to one another in a manner that enables them to be detected by the inductive distance sensor.

The hydrometer float can comprise a graduated ruler (scale) having indicia corresponding to specific gravity values. The graduated ruler can be along and/or embedded in the exterior surface of the shaft of the hydrometer float, for example, as found in a typical, traditional (analog) hydrometer that heretofore was read directly by eye at the surface of the liquid being measured for specific gravity. If the hydrometer float is transparent, the graduated ruler can be on or embedded in an interior surface of the hydrometer float.

A traditional hydrometer often includes a ballast that can be or include a metallic object, for example, mercury. In such cases, a traditional hydrometer can be used directly as the hydrometer float of the digital hydrometer of the present invention. In cases in which the traditional hydrometer cannot be adequately detected by the inductive distance sensor, the traditional hydrometer can be modified by applying one or more metallic objects so that it can be detected. The metallic object can be applied as a coating, a foil, a wound wire, or the like. The metallic object can be applied using an adapter module that contains one or more metallic objects. For example, an induction adapter module can be used that comprises the metallic object and is configured to attach at the bottom end of the hydrometer float. The induction adapter module can be attached to the hydrometer float by any suitable means, for example, suction, adhesion, a friction fit, a snap-fit, a screw fit, a clamp fit, a luer fit, or a combination thereof.

Any suitable displacement vessel can be used with the digital hydrometer. The displacement vessel can be customized for use with the hydrometer base or can be an off-the-shelf container capable of holding the displacement fluid and hydrometer float. The displacement vessel can be graduated or ungraduated, that is, it can include or lack a ruler for volume or other measurement. For example, the displacement vessel can include one or more demarcations such as fill lines that indicate the level to which the vessel should be filled with a test or calibration standard liquid. The demarcation line or lines can be solid, continuous, dashed, dotted, or otherwise broken, for example, a fill line can occur at spaced intervals around the circumference of the displacement vessel. The displacement vessel can have any suitable geometry with respect to size, shape, and/or volumetric capacity. For example, the displacement vessel can have a hollow cylindrical shape, an interior, an interior diameter, a top end, and an opening to the interior at the top end. The hydrometer float can comprise a maximum outer diameter that is at least slightly smaller than the interior diameter of the displacement vessel, to enable vertical movement. For example, the maximum outer diameter can be smaller than the interior diameter by a distance of from one millimeter to ten millimeters. The hydrometer float can have a length, a maximum outer diameter, and a ratio of the length to the maximum outer diameter of from about 2:1 to about 20:1.

The displacement vessel can further include a lid. The lid can include a central aperture that enables vertical movement of at least a portion, for example, the stem, of the hydrometer float through the lid. The lid and the central aperture can aid in centering the hydrometer float in the displacement vessel. The displacement vessel can be emptied by any suitable method and/or apparatus. The liquid can be poured from or siphoned out through the lid or opening at the top of the displacement vessel. Alternatively, the displacement vessel can be equipped with a drain at or near the bottom of the displacement vessel. The digital hydrometer base can optionally include suitable plumbing for assisting in draining the displacement vessel.

The displacement fluid, for example, liquid contained in the displacement vessel, can be any suitable liquid, for example, a test liquid, a control liquid, or a calibration standard liquid. The calibration standard liquid can be a liquid of known specific gravity. A set or kit of one or more calibration standard liquids can be supplied and/or used with the digital hydrometer. A plurality of calibration standard liquids can be used, for example, three calibration standard liquids having relative low, medium, and high specific gravities. The specific gravities of the calibration standard liquids can be selected for distribution about or near a target specific gravity or range. The calibration standard liquid can be used to produce a suitable curve or slope for determining the specific gravity of a test liquid. For example, the graph (curve) or slope can be determined from the relationship between specific gravity and an impedance, a change in impedance, or a distance measured, using the inductive distance sensor. The calibration curve can be displayed on a video display. One or more specific gravity measurements can be superimposed on the calibration curve for visual inspection of their location relative to the curve.

The displacement fluid contained in the displacement vessel can be or comprise a dialysate or a dialysate concentrate. The test liquid and/or a calibration standard liquid can be the displacement fluid. For example, the test liquid can be a newly mixed acid concentrate batch and the calibration standard liquid can be a previous acid concentrate batch of known and desired specific gravity. Saline or salt water can be used as one or more calibration standard liquids.

A method of calculating a specific gravity of a test liquid is provided by the present invention. The method can be performed using a digital hydrometer of the present invention. For example, a method of calculating a specific gravity of a test liquid can include the following steps. A first measured amount of the test liquid can be placed in a displacement vessel, the top of the liquid defining a liquid surface. A hydrometer float can be floated in the test liquid in the displacement vessel. The hydrometer float can comprise a metallic object configured to change the impedance produced by an inductor (of an inductive distance sensor) by an amount that varies based on the proximity of the metallic object to the inductor. The hydrometer float can comprise a top end and a bottom end. The hydrometer float can have a buoyancy that causes the top end to extend above the liquid surface and the bottom end to be submerged in the test liquid below the liquid surface. An impedance caused by the proximity of the metallic object to the inductor can be measured. The specific gravity of the liquid can be calculated by converting the impedance to a corresponding specific gravity value. A base impedance can be measured before floating the hydrometer float. The conversion can be performed via a difference in impedance caused by the metallic object relative to the base impedance. The calculating can comprise converting the measured impedance to a distance value, representing a linear displacement between the metallic object and the inductor, and then converting the distance value to a corresponding specific gravity value. The calculating can comprise using a pre-determined calibration curve, a slope, a standard table, or a formula. The curve, slope, table, or formula can be based on or normalized to the metallic object used to measure the change in impedance caused by its buoyancy in the test liquid.

One or more calibration procedures can be performed before, during, or after measuring the impedance of a test liquid and/or the calculation of its specific gravity. For example, the method can further comprise one or more of the following steps. The test liquid can be emptied from the displacement vessel. A second measured amount of a calibration standard liquid having a known specific gravity can be placed in the displacement vessel. The hydrometer float can be floated in the calibration standard liquid in the displacement vessel. The impedance caused by the proximity of the metallic object to the inductor while the hydrometer float is floating in the calibration standard liquid in the displacement vessel can be measured. The second measured amount can be the same as the first measured amount. The calculating can comprise comparing the impedance measured by floating the hydrometer float in the test liquid in the displacement vessel with the impedance measured by floating the hydrometer float in the calibration standard liquid in the displacement vessel.

More than one calibration standard liquid can be used. For example, the method can comprise one or more the following steps. The displacement vessel can be emptied of the test liquid. A second measured amount of a first calibration standard liquid having a known specific gravity can be placed in the displacement vessel. The hydrometer float can be floated in the first calibration standard liquid in the displacement vessel. The change in impedance caused by the proximity of the metallic object to the inductor while the hydrometer float is floating in the first calibration standard liquid in the displacement vessel can be measured. The first calibration standard liquid can be emptied from the displacement vessel. A third measured amount of a second calibration standard liquid having a known specific gravity can be placed in the displacement vessel. The hydrometer float can be floated in the second calibration standard liquid in the displacement vessel. The change in impedance caused by the proximity of the metallic object to the inductor while the hydrometer float is floating in the second calibration standard liquid in the displacement vessel can be measured. The second calibration standard liquid can be emptied from the displacement vessel. A fourth measured amount of a third calibration standard liquid having a known specific gravity can be placed in the displacement vessel. The hydrometer float can be floated in the third calibration standard liquid in the displacement vessel. The change in impedance caused by the proximity of the metallic object to the inductor while the hydrometer float is floating in the third calibration standard liquid in the displacement vessel can be measured. A calibration curve can be generated based on the changes in impedance measured using the first, second, and third calibration standard liquids. The first, second, third, and fourth measured amounts of liquid, i.e., the volume of each, can be substantially the same, for example, exactly the same. The calculating can comprise comparing the change in impedance measured by floating the hydrometer float in the test liquid with the calibration curve, for example, the slope of, points along, or another parameter of the calibration curve can be used for comparison purposes, or a formula based on the calibration curve can be used.

The test liquid measured in the method can comprise any liquid for which a specific gravity is sought. For example, the test liquid can comprise an acid concentrate (batch) and the method can further comprise one or more of the following steps. The specific gravity calculated for the dialysate can be compared to a target specific gravity value or to a range of acceptable specific gravities. It can be determined whether or not the specific gravity of the dialysate is sufficiently close to the target value or within an acceptable range. For example, it can be determined whether or not the specific gravity is within a particular standard deviation from an average target value.

After determining a dialysate is of an acceptable specific gravity, a dialysis circuit of a dialysis machine can be filled or primed with the dialysate. The test liquid can comprise a dialysate, a dialysate batch, or a dialysate concentrate batch and the method can comprise one or more of the following steps. The specific gravity calculated for the batch or liquid to be tested can be compared with a target value or an acceptable range of values. It can be determined whether or not the specific gravity of the batch or liquid is sufficiently close to the target value or within an acceptable range. The batch or liquid can then be labeled as being acceptable to use if the specific gravity is sufficiently close to the target value or within the acceptable range. A batch of any type of dialysate concentrate can be measured. For example, the dialysate concentrate batch can comprise an acid or base concentrate.

For consistency in measurements of impedance and/or distances corresponding to a given impedance or change in impedance, it is desirable to use a consistent volume of displacement fluid. This consistency can be achieved by premeasuring a volume before placement in the displacement vessel or by using a demarcation or fill line indicated on or transparently through a surface of the displacement vessel. Accordingly, the placing of a first or subsequent measured amount can comprise filling the displacement vessel so that the liquid surface rests at a predetermined demarcation on or in the displacement vessel.

The specific gravity calculated for a particular test liquid can be displayed on a digital display. The display of the value of specific gravity can be displayed using any number of digits, for example, a number of digits rounded to the relevant number of significant figures. If multiple measurements and calculations are made, a standard deviation can be displayed. The calculated specific gravity can be displayed intermittently or concurrently with a target specific gravity value or range. A difference between the calculated and target specific gravity can also be digitally displayed. If a calculated specific gravity is acceptable or otherwise in range, a text, symbol, or sound can be generated indicating the same. For example, an LED indicator can light or flash green, for a passing grade or value, and red for a failing grade or value, depending on whether or not the specific gravity calculated in acceptable.

FIG. 1 is a perspective view of a system 10 including a digital hydrometer 20 and related components in accordance with the present invention. Digital hydrometer 20 includes a digital hydrometer base 22 and a displacement vessel 24 atop digital hydrometer base 22. A test liquid 26 is shown loaded as a displacement fluid in displacement vessel 24. Test liquid 26 can be an aliquot from a prepared acid concentrate batch 28 shown in a beaker. A hydrometer float 30 floats in displacement vessel 24, which is capped by a vessel lid 32 through which the stem of hydrometer float 30 passes. A plurality of calibration standard liquids 34 are depicted including a first calibration standard liquid 36, a second calibration standard liquid 38, and a third calibration standard liquid 40, corresponding to displacement fluids of known, relatively high, medium, and low specific gravities respectively, which can be used to calibrate digital hydrometer 20. An optional data wire 42 is shown connecting digital hydrometer base 22 to an external device 44, which can transfer data relating to impedance measurement data, distance data, and/or calculated specific gravity data.

Figure 2:
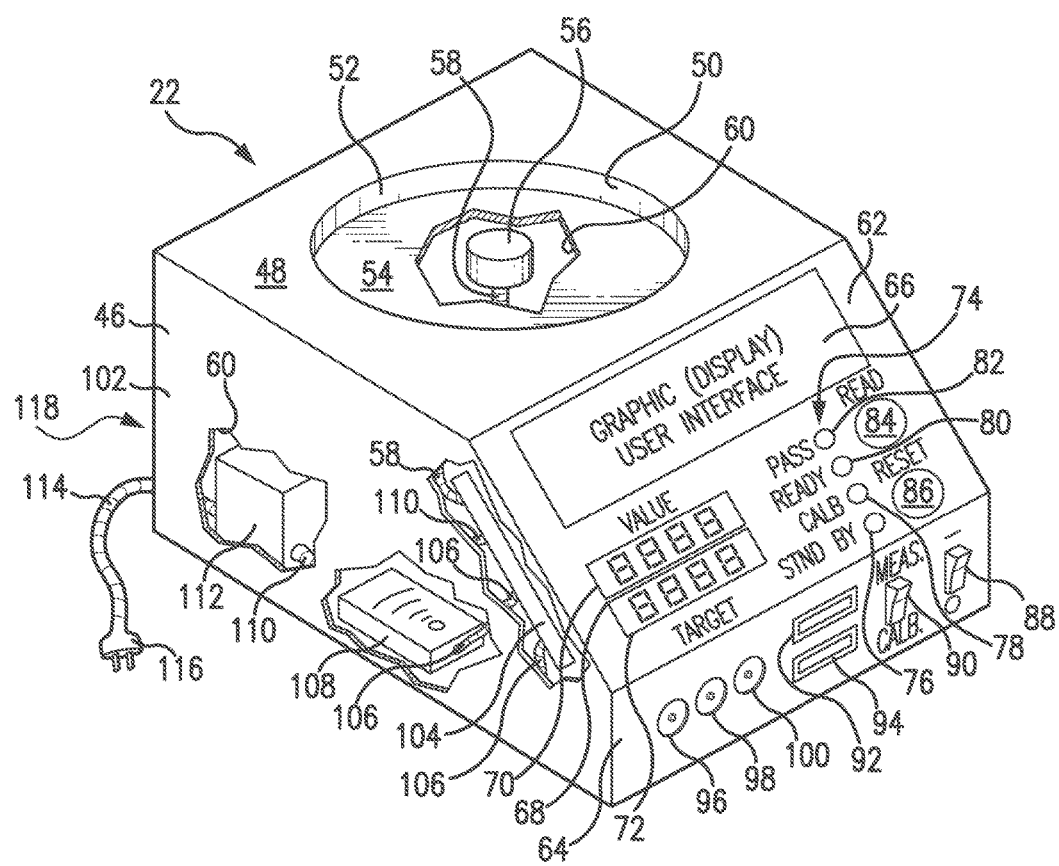
FIG. 2 is an enlarged perspective view of the digital hydrometer base shown in FIG. 1.

FIG. 2 is an enlarged perspective view of digital hydrometer base 22 shown in FIG. 1. Digital hydrometer base 22 has a base housing 46 including a base top surface 48 configured to support displacement vessel 24 shown in FIG. 1. Base top surface 48 can be set in a common plane as a flat continuous surface, but, as shown in FIG. 2, includes a base recess 50 that helps position and retain displacement vessel 24. Alternatively or additionally, a raised ridge and/or other components, for example, a tray accessory, can extend from base top surface 48 about an outer circumference of displacement vessel 24. Base recess 50 includes a recess sidewall 52 extending downward from base top surface 48, or inside an inner rim and a recess floor 54. The shape and size of recess sidewall 52 and recess floor 54 can be provided to complement that of displacement vessel 24. Although not shown in FIG. 2, base recess 50 can further include a locking mechanism, for example, a suction cup, a snap-fit hook, one or more bolts, or circumferential screw threading, to help retain displacement vessel 24. Displacement vessel 24 can optionally include corresponding locking elements, for example, a snap fit notch, bolt holes, or complementary threading to function with the optional locking mechanism of base recess 50. As shown in FIG. 2, base recess 50 can retain displacement vessel through a simple friction fit.

An inductive distance sensor 56 is shown through the cut-away view of recess floor 54. Inductive distance sensor 56 and/or induction circuit 58 can be contained in base interior 60 to help shield them from spilled displacement fluid or other materials. Alternatively, inductive distance sensor 56 can be located on or extend through recess floor 54 or another portion of base top surface 48. Induction circuit 58 can integrate and operatively connect inductive distance sensor 56 with other electronics in digital hydrometer base 22 and/or external circuitry.

Base housing 46 can include one or more surfaces that provide elements that enable a user to interface with digital hydrometer 20 and/or transfer data to and from digital hydrometer 20. As shown in FIG. 2, base housing 46 includes a base front interface surface 62 and a base front access surface 64. Depending, for example, on the shape of digital hydrometer base 22, these two surfaces can form a single surface or be otherwise situated while still retaining their functionality.

Base front interface surface 62 can include any number or kind of displays capable of displaying a specific gravity value in digital form. As shown in FIG. 2, base front interface surface 62 includes a video display 66 and a digital display 68. Video display 66 can be omitted, but, if included, can complement digital display 68 and can act as a graphical user interface (GUI), for example, provided with touchscreen elements. One or both displays can alternatively be located as part of an external device in communication with digital hydrometer base 22.

As shown in FIG. 2, digital display 68 is depicted, for example, as a seven-segment display divided into a value (measurement) display 70 and an optional target display 72. Value display 70 can be configured to display a specific gravity value of a test or calibration standard liquid measured and calculated using digital hydrometer 20. Target display 72 can be configured to display a target specific gravity value that is sought for a test liquid, or the difference between the measured specific gravity value of a test liquid and a target value.

Base front interface surface 62 can include further elements as shown in FIG. 2, which can aid the user in interfacing with digital hydrometer 20. Such further elements can be omitted in whole or part depending, for example, on whether or not other interface means are utilized. For example, other elements might not be needed if video display 66 is a touchscreen and/or if one or more external devices or peripherals such as a mouse, keyboard, and/or connected personal computer or network are utilized. A plurality of indicator lights 74 can be included. For example, and as shown in FIG. 2, the plurality can include a first indicator light 76, a second indicator light 78, a third indicator light 80, and a fourth indicator light 82. Each light can be, for example, an LED or combination of LEDs, such as a combination of green and red LEDs, or green, red, and yellow LEDs. Each light can signify information, for example, the status of the machine or the acceptability of a specific gravity measurement. For example, first indicator light 76 is shown as a "standby" indicator signifying that digital hydrometer 20 is warming-up or in the middle of performing a measurement, calculation, or other operation. Second indicator light 78 is shown as signifying a calibration mode during which digital hydrometer 20 is being calibrated. Third indicator light 80 is shown as a "ready" indicator signifying that digital hydrometer 20 is ready to take a measurement (and optionally calculate a specific gravity value based on the same). Fourth indicator light 82 is shown as a "pass" indicator signifying that the specific gravity measured and calculated has passed, that is, is sufficiently close to a target value or within a range of acceptable specific gravity values.

Base front interface surface 62 also includes a first (read) button 84 and a second (reset) button 86. Either or both buttons can be omitted if their functionalities are incorporated into another user interface, for example, video display 66. First button 84 can be configured to initiate an impedance measurement for determining a specific gravity of a test liquid or a corresponding impedance for a calibration standard liquid. Second button 86 can be configured to clear out the working memory, for example, a RAM, and return digital hydrometer 20 to a beginning state as when it is initially turned on.

Base front access surface 64 includes a power switch 88 and a mode switch 90, which are shown, for example, as toggle switches. Power switch 88 is configured to turn digital hydrometer 20 on and off. Mode switch is configured to switch between a calibration mode for calibration of the digital hydrometer, and a measurement mode for measuring the specific gravity of a test liquid. As with other components, the location of these switches can be different. For example, power switch 88 can be located on a lateral side, top, or back side of digital hydrometer base 22, and mode switch 90 can be located on base front interface surface 62 or omitted altogether if mode is controlled through a different interface, for example, through video display 66.

Base front access surface 64 can include any number or types of data ports. One or all of these data ports can be located elsewhere on digital hydrometer base 22, for example, on a back surface. First universal data port 92 and second universal data port 94 can be configured to receive universal serial bus (USB) cables. First accessory data port 96, second accessory data port 98, and third accessory data port 100 can be configured to receive coaxial data lines. Any or all of these data ports can be used to connect to external devices that utilize data from digital hydrometer 20, for example, external device 44, or other peripherals, for example, various user interfaces or control apparatuses. Such user interfaces can include, for example, a smart phone, a touchscreen tablet, a mouse, a keyboard, a receiver, a transmitter, or the like. An example of a peripheral is a barcode or RFID reader for reading codes on reagent containers such as those holding calibration standard liquids, or on an operation card or manual for a medical device, for example, a dialysate machine or dialysate mixer.

Several cut-aways of base lateral side 102 of digital hydrometer base 22 reveal components located in base interior 60. For example, a printed circuit board (PCB) 104 is shown that can be configured to connect to the various elements of the base front interface surface 62 and base front access surface 64, as well as other electronic/data/power circuits and components of digital hydrometer 20. An output circuit 106 is shown connected to PCB 104, which can connect inductive data sensor 56 to digital display 68 and other components and circuits including, for example, one or more of the data ports for wired connections or wireless transmitter 108 for wireless connections. A power circuit 110 is shown that can be in electronic communication with power switch 88 as well as a power source (converter) 112, a power cable 114, and a plug 116 for interface with a wall outlet, remote power source, or other power outlet. Disposable batteries, rechargeable batteries, or the like can also be used as the power source or as a back-up power supply. Power cable 114 can extend from, for example, a back surface 118 of digital hydrometer base 22. Power circuit 110 can provide power to the other circuits of digital hydrometer 20.

Figure 3A:
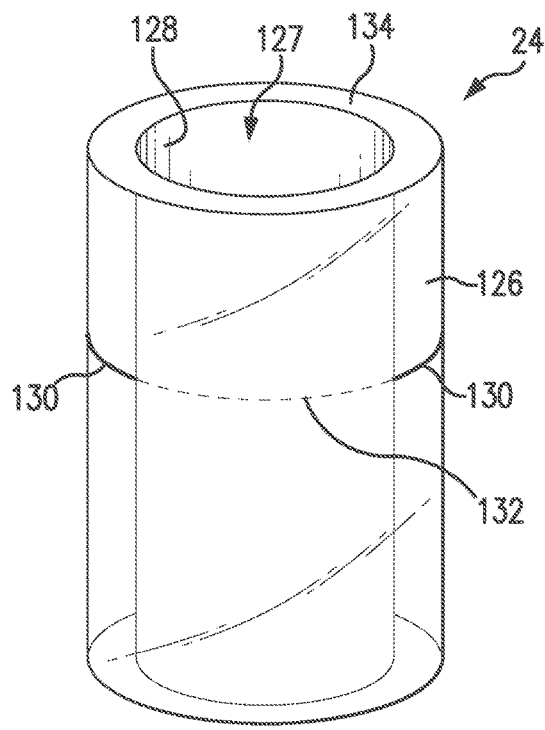
FIG. 3A is an enlarged perspective view of the displacement vessel shown in FIG. 1.
Figure 3B:
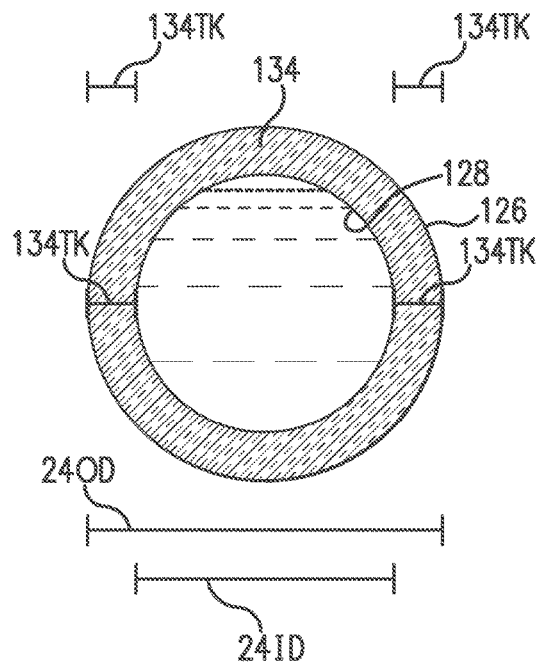
FIG. 3B is a top (plan) view of the displacement vessel shown in FIG. 3A.

FIG. 3A is an enlarged perspective view of displacement vessel 24 shown in FIG. 1. Displacement vessel 24 has a vessel exterior 126 and a vessel interior 128. A demarcation (fill) line 130 is located on vessel exterior 126, but can alternatively or additionally be located on vessel interior 128. Demarcation line 130 can indicate to what level displacement vessel 24 should be filled with a displacement fluid so that a liquid surface 132 of the displacement fluid rests at demarcation line 130. Vessel exterior 126 and vessel interior 128 help define a vessel wall 134 and a vessel opening 127. FIG. 3B is a top (plan) view of the displacement vessel shown in FIG. 3A. Vessel wall thickness 134TK is defined by vessel outer diameter 240D and vessel inner diameter 24ID. Vessel inner diameter 24ID is wide enough to enable vertical passage of hydrometer float 30. Vessel outer diameter 240D is narrow enough to allow for insertion into base recess 50.

Figure 4A:
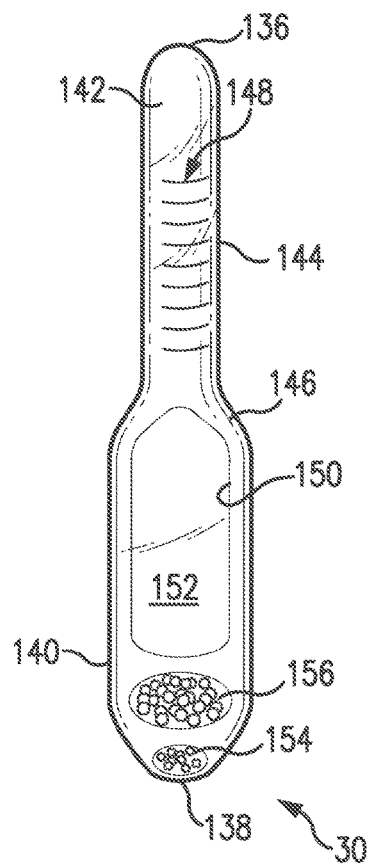
FIG. 4A is a side view of the hydrometer float shown in FIG. 1.

FIG. 4A is a side view of hydrometer float 30 shown in FIG. 1. Hydrometer float 30 has a top end 136 and a bottom end 138. Hydrometer float 30 comprises a bulb 140 proximal and extending from bottom end 138 toward top end 136, and having a bulb diameter 140D sufficiently narrow to pass vertically through displacement vessel 24. Hydrometer float 30 comprises a stem 142 proximal and extending from top end 136 toward bottom end 138, and having a stem diameter 142D that is sufficiently narrow to pass through the hole in lid 32. Stem 142 can extend seamlessly and/or continuously from bulb 140. A hydrometer float in accordance with the present invention need not have discernable bulb and stem portions as shown in the example of hydrometer float 30.

Figure 4B:
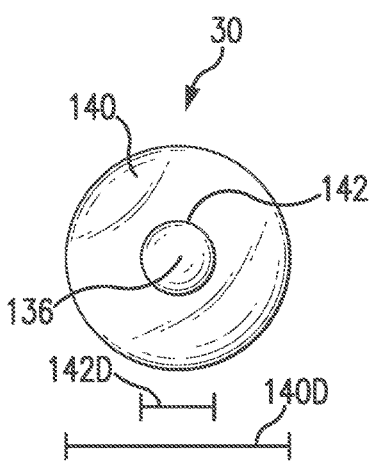
FIG. 4B is a top (plan) view of the hydrometer float shown in FIG. 4A.

Hydrometer float 30 can comprise an exterior surface 144 and an interior 146. A graduated ruler 148 can be included along the length of hydrometer stem 142 demarcating specific gravity values as in a traditional analog hydrometer. Hydrometer float 30 comprises a chamber 150 within interior 146. Chamber 150 can comprise a gas 152 to help provide buoyancy to hydrometer float 30. Hydrometer float 30 can comprise a ballast 154 in hydrometer interior 146 proximal bottom 138 to help maintain hydrometer float 30 in an upright position. Hydrometer float 30 can comprise a metallic object 156, capable of detection by inductive distance sensor 56, in interior 146, proximal to bottom 138. Ballast 154 and metallic object 156 can be separate elements or can be the same element. That is, a single element can serve as both ballast 154 and metallic object 156, for example, a mass of iron and/or other metal. FIG. 4B is a top (plan) view of hydrometer float 30 shown in FIG. 4A. As shown in FIG. 4B, bulb 140 has a maximum outer diameter denoted as 140D and stem 142 has a maximum outer diameter denoted as 142D.

Figure 5:
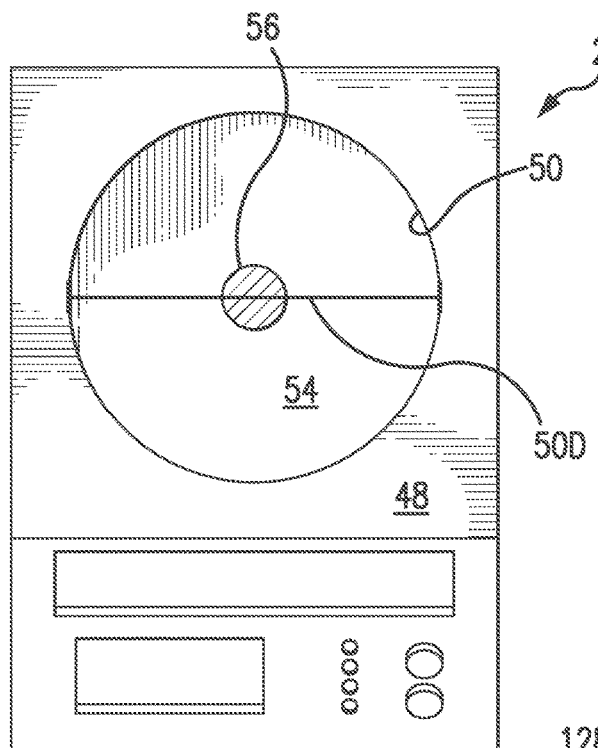
FIG. 5 is a top (plan) view of the digital hydrometer base shown in FIG. 2.
Figure 6:
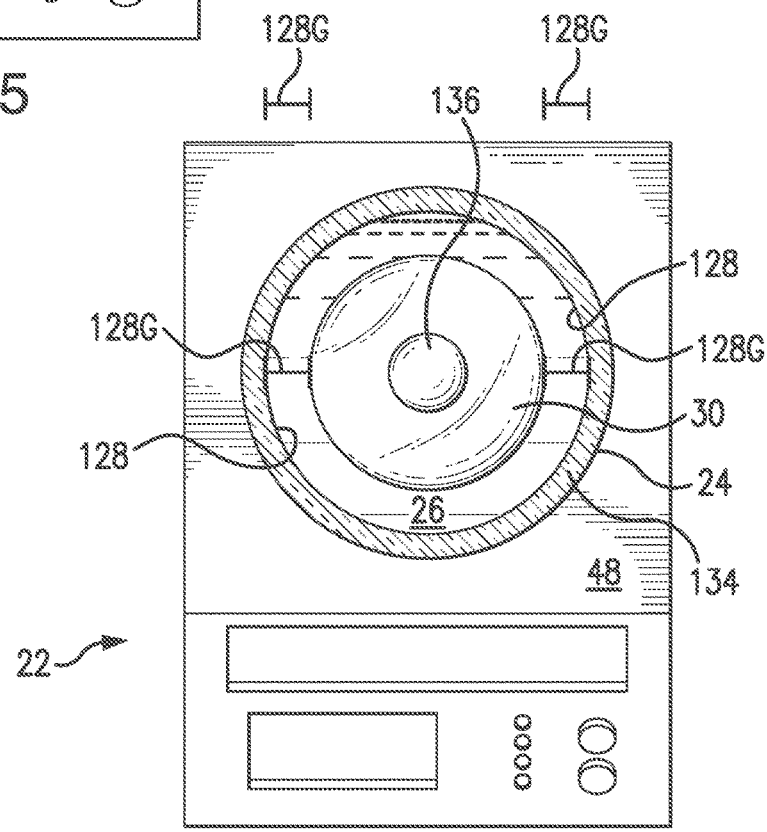
FIG. 6 is a top (plan) view of the digital hydrometer base shown in FIG. 2 and holding a displacement vessel and a test liquid with a hydrometer float floating therein, in accordance with the present invention.

FIG. 5 is a top (plan) view of digital hydrometer base 22 shown in FIG. 2. Recess 50 has a recess diameter 50D that is sufficiently wide to enable insertion of the bottom end of displacement vessel 24. FIG. 6 is a top (plan) view of digital hydrometer base 22 holding displacement vessel 24, a test liquid 26, and hydrometer float 30 floating therein, in accordance with the present invention. A vessel-hydrometer gap 128G exists between interior surface 128 of the vessel wall and hydrometer float 30 to enable vertical movement of hydrometer float 30. FIG. 6 shows a view without lid 32 being present in order to show the optional use of vessel lid 32 and also to show vessel-hydrometer gap 128G.

Figure 7A:
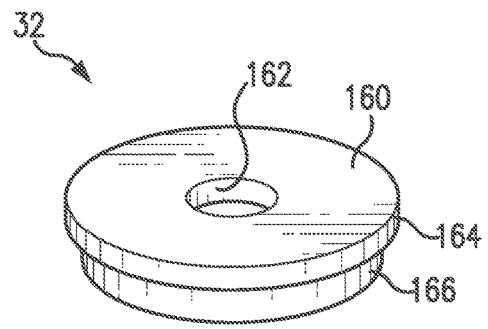
FIG. 7A is a front perspective view of the vessel lid shown in FIG. 1.
Figure 7B:
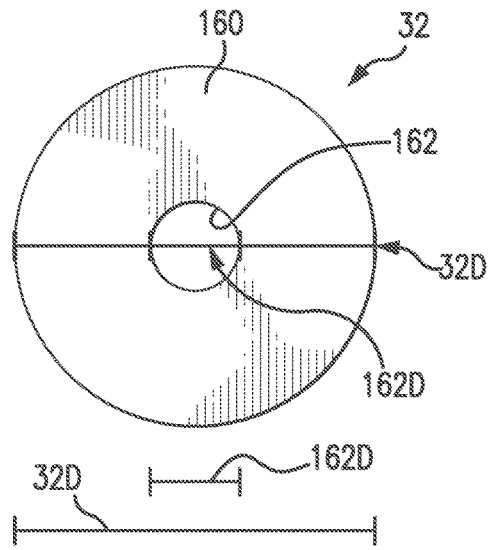
FIG. 7B is a top view of the vessel lid shown in FIG. 7A.
Figure 7C:
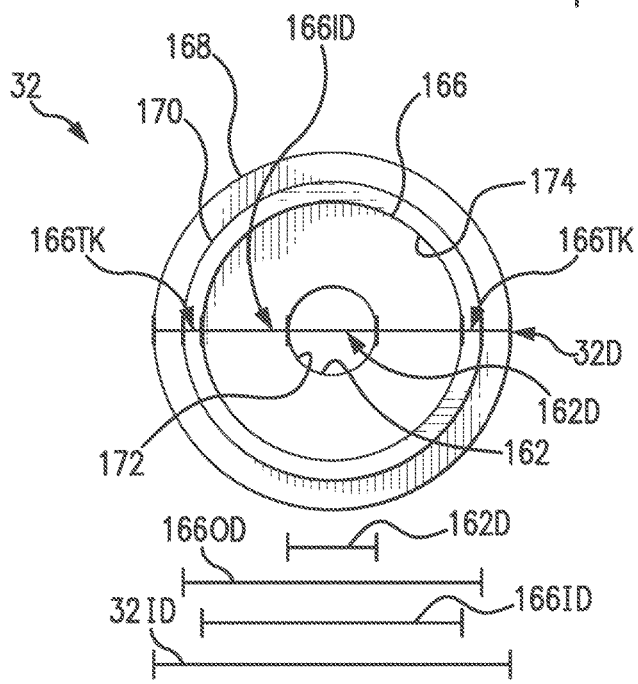
FIG. 7C is a bottom view of the vessel lid shown in FIG. 7A.

FIG. 7A is a front perspective view of vessel lid 32 shown in FIG. 1. Lid 32 comprises a lid aperture 162 at its center. Vessel lid 32 also comprises a lid horizontal flange 164 and a lid vertical flange 166, the latter of which helps retain and center lid 32 in displacement vessel opening 127. FIG. 7B is a top view of vessel lid 32 shown in FIG. 7A. Vessel lid 32 has a diameter 32D and an aperture diameter 162D. Aperture diameter 162D is sufficiently wide to enable vertical passage of hydrometer stem 142. FIG. 7C is a bottom view of vessel lid 32 shown in FIGS. 7A and 7B. FIG. 7C shows lid horizontal flange 164 having a horizontal flange outer edge 168, lid vertical flange 166 having a vertical flange outer edge 170, and lid aperture 162 having an aperture edge 172. Lid vertical flange 166 also has a vertical flange inner edge 174. Vertical flange outer edge 170 defines a vertical flange outer diameter 166OD. Vertical flange inner edge 174 defines a vertical flange inner diameter 166ID. Vertical flange outer and inner diameters 166OD and 166ID define a vertical flange thickness 166TK. Vertical flange outer diameter 166OD is sufficiently narrow to enable insertion of vessel lid 32 into displacement vessel opening 127.

Figure 8:
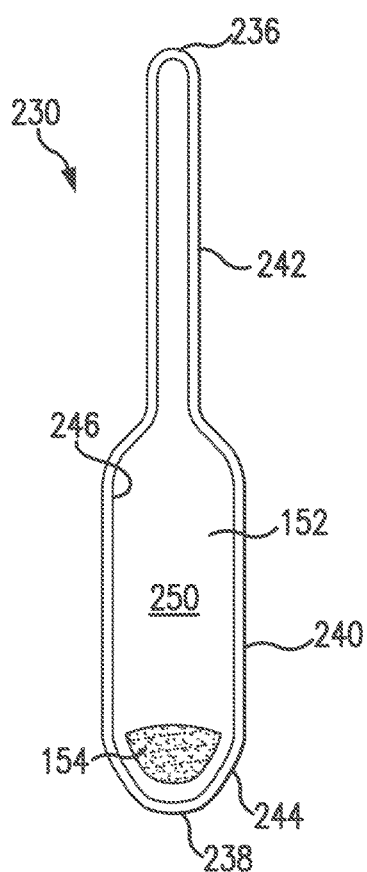
FIG. 8 is a cross-sectional view of another hydrometer float in accordance with the present invention.

FIG. 8 is a cross-section view of a second hydrometer float 230 in accordance with the present invention. Second hydrometer float 230 is similar in many respects to hydrometer float 30, but lacks a metallic object 156 that would enable second hydrometer float 230 to be readily and accurately sensed by inductive digital sensor 56. Second hydrometer float 230 has a second top end 236 and a second bottom end 238. Second hydrometer float 230 comprises a second bulb 240 proximal to second bottom end 238 and extending toward second top end 236. Second hydrometer float 230 comprises a second stem 242 proximal to second top end 236 extending toward second bottom end 238. Second hydrometer float 230 comprises a second exterior surface 244 and a second interior 246. Second hydrometer float 230 comprises a second chamber 250 in second interior 246. Second chamber 250 is shown extending from second bulb 240 into second stem 242, as an example, but can be restricted to second bulb 240 analogous to the embodiment shown for chamber 150 in hydrometer float 30. Second chamber 250 can contain gas 152 for providing buoyancy.

Figure 10:
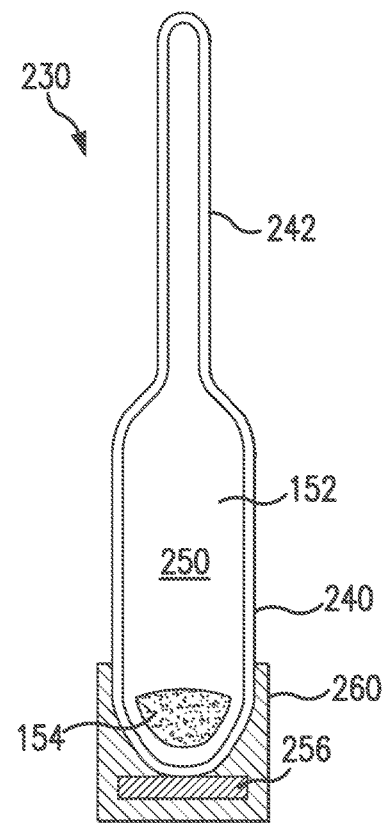
FIG. 10 is a cross-sectional view of the hydrometer float shown in FIG. 8 connected to the hydrometer float adapter shown in FIG. 9C.
Figure 9A:
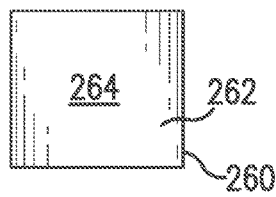
FIG. 9A is a side view of a hydrometer float adapter in accordance with the present invention.
Figure 9B:
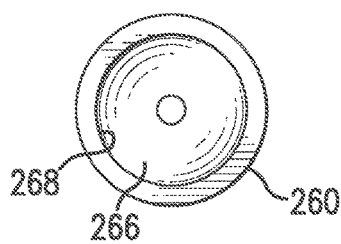
FIG. 9B is a top (plan) view of the hydrometer float adapter shown in FIG. 9A.
Figure 9C:
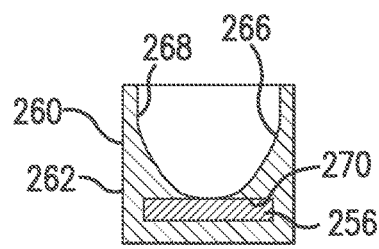
FIG. 9C is a cross-sectional view of the hydrometer float adapter shown in FIGS. 9A and 9B.

FIG. 9A is a side view of a hydrometer adapter module 260 in accordance with the present invention. Hydrometer adapter module 260 comprises an adapter housing 262 and an adapter exterior surface 264. FIG. 9B is a top (plan) view of hydrometer adapter 260 shown in FIG. 9A. Hydrometer adapter module comprises an adapter interior surface 266 within an adapter recess 268 complementary to second bottom end 238. FIG. 9C is a cross-section view of hydrometer adapter module 260 shown in FIGS. 9A and 9B. Hydrometer adapter module 260 comprises a metallic object 256, detectable by inductive distance sensor 56, located in an adapter interior cavity 270. FIG. 10 is a cross-sectional view of second hydrometer float 230 shown in FIG. 8 connected to hydrometer adapter module 260 shown in FIGS. 9A-9C.

Figure 11:
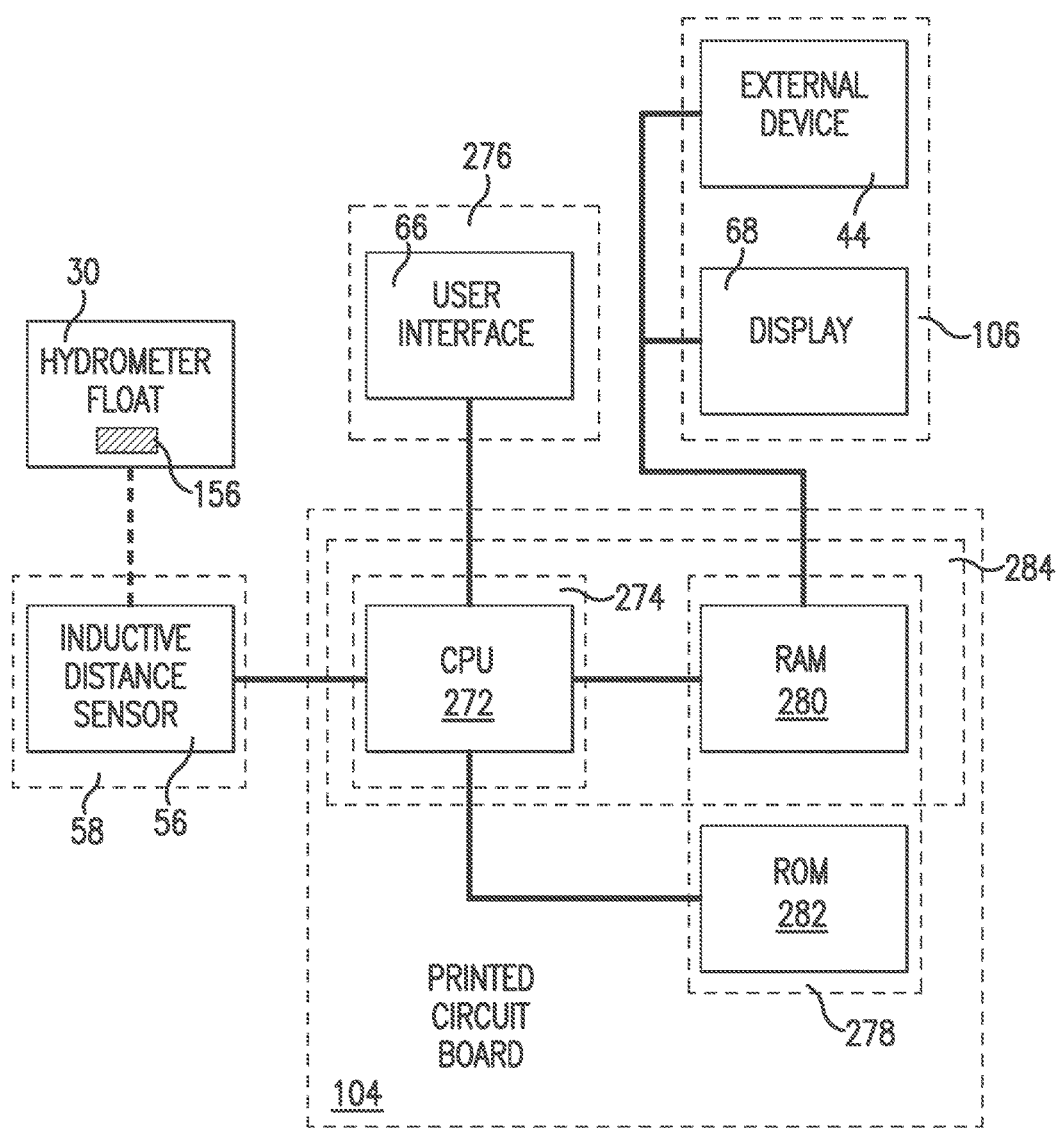
FIG. 11 is a schematic diagram showing the connectivity of an exemplary system and digital hydrometer, in accordance with the present invention.

FIG. 11 is a schematic diagram illustrating the connectivity of system 10 and the digital hydrometer 20, in accordance with the present invention. Inductive distance sensor 56 is shown as part of an induction circuit 58 and its relationship, at a distance, with metallic object 156 of hydrometer float 30. Impedance data obtained from inductive distance sensor 56 can be transferred from induction circuit 58 to a central processing unit (CPU/computer) 272 of a processor circuit 274 in order to calculate a specific gravity value. A control circuit 276 can include or be connected to a user interface, for example, video display 66, to enable a user to control system 10 and/or digital hydrometer 20. Control circuit 276 can be in communication with induction circuit 58 via CPU 272 as shown, and/or directly to induction circuit 58. A memory circuit 278 can include a random access memory (RAM) 280 and a read only memory (ROM) 282. Memory circuit 278 can also include one or more external memories, for example, a thumb drive inserted into first universal data port 92 or second universal data port 94, or a hard drive connected through first, second, or third accessory data ports 96, 98, and 100, shown in FIG. 2. Memory circuit 278 is connected to processor circuit 274 and output circuit 106. Output circuit 106 can include or be connected to external device 44, digital display 68, or another suitable destination, to enable impedance data, change in impedance data, and/or calculated specific gravity values to be displayed and stored. Calibration circuit 284 can include CPU 272 and RAM 280 to enable impedances measured for calibration standard liquids of known specific gravity values to be stored, accessed, and used to calculate a calibration curve or data table for, in-turn, calculating specific gravity values for unknown test liquids. Printed circuit board 104 (FIG. 2) can collectively include processor circuit 274, memory circuit 278, and calibration circuit 284 on a common motherboard. Alternatively, one or more of these circuits can be included on one or more separate boards.

Figure 12:
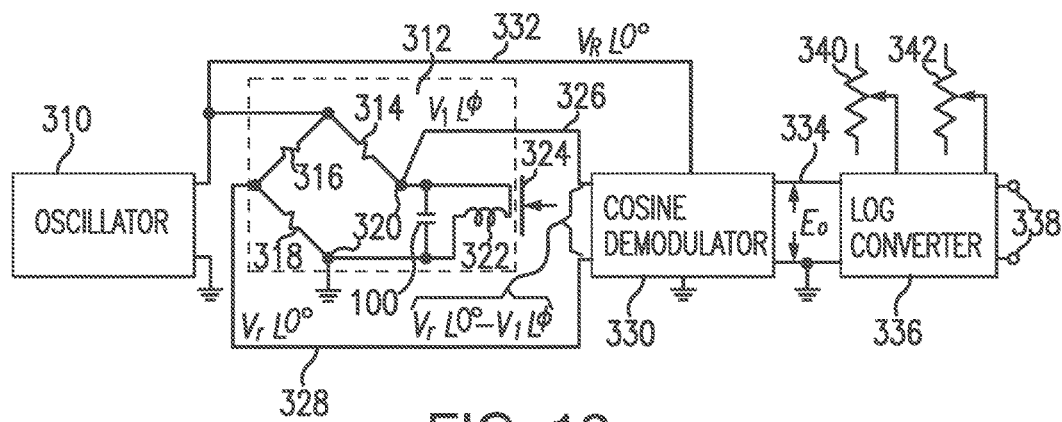
FIG. 12 is a diagram of an induction circuit including an inductive transducer usable in accordance with the present invention.
Figure 13:
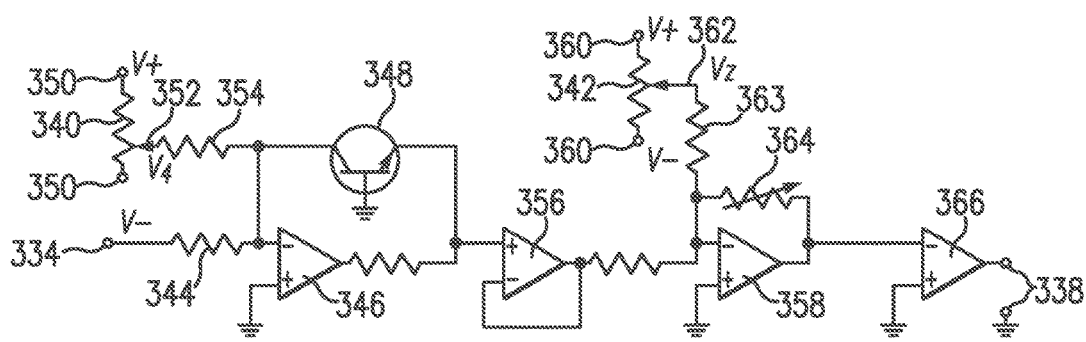
FIG. 13 is a schematic diagram of one of the components shown in FIG. 12.

An example of an inductive distance sensor and inductive circuit suitable for use in the present invention is described in U.S. Pat. No. 4,160,204, which is hereby incorporated by reference herein in its entirety. Accordingly, FIG. 12 is a diagram of an induction circuit including an inductive transducer usable in accordance with the present invention. FIG. 13 is a schematic diagram of one of the components shown in FIG. 12. The embodiment shown in FIG. 12 is illustrated partially in block diagram form and with certain portions showing a detailed arrangement of circuit elements to specifically illustrate the sensor. The system includes a high frequency signal source 310 such as a conventional and well-known oscillator. The source 310 is connected to and provides a signal phase network 312, which may be, for example, an electronic bridge illustrated as having branches 314, 316, 318, and 320. Branch 320 represents a distance-related impedance because connected to and forming a part of branch 320 is a transducer such as a single coil inductor 322. As will subsequently be described more fully, inductor 322 provides an impedance that varies in relation to the proximity of a metal object 324, and in so doing varies the impedance of branch 320. Branch 318 serves as a reference impedance for comparing signal changes across branch 320 caused by the impedance change of the transducer 322. Branches 314, 316, and 318 are of fixed, known impedance, and conveniently may be fixed-value resistors.

Conductors 326 and 328 connect a cosine demodulator 330 to the signal phase network 312. Conductor 326 transmits a signal from branch 320 related to the impedance of the transducer or single coil inductor 322. A reference signal is supplied by conductor 328 from the reference impedance of branch 318. The signals appearing on conductors 326 and 328 form inputs to the cosine demodulator 330, otherwise known as a differential input phase sensitive demodulator, and these signals are of identical frequency but may have a relative magnitude and phase difference with respect to each other. The magnitude and phase difference will vary as a result of the variation in impedance of the inductive transducer 322 during distance measurement, when compared to the non-varying impedance of the reference impedance of branch 318. The cosine demodulator 330 will provide a DC output signal on conductor 334, which varies according to Equation 1 below:

$$E_o = V_r \cos \theta - V_1 \cos \varphi \quad \text{(Equation 1)}$$

where $E_o$ is the DC output signal appearing on conductor 334, $V_r$ is the magnitude of the signal appearing on the conductor 328, theta is the phase angle of the signal appearing on conductor 328 with respect to the signal appearing on conductor 332, $V_1$ is the magnitude of the signal appearing on conductor 326, and phi is the phase angle of the signal appearing on conductor 326 with respect to the signal appearing on conductor 332. Conductor 332 supplies a phase reference signal, $V_r$ 10°, from the source 310 to the cosine demodulator 330, which is used for the determination of the cosine of the phase angle of the two input signals. Where 316 and 318 are fixed resistors and theta is 0°, (Equation 1) then becomes (Equation 1A) as follows:

$$E_o = V_r - V_1 \cos \varphi \quad \text{(Equation 1A)}$$

The signal appearing on conductor 334 is essentially logarithmic in character. A log convertor 336 is used to change the logarithmic signal to a linear signal and to supply the linear signal to the output terminals 338. Variable resistances 340 and 342 are used to bias the convertor 336 thereby aiding in securing an extremely high degree of linearity during the measurement process as will be described subsequently in conjunction with FIG. 13.

In FIG. 13, the specific circuit of the modified log convertor 336 is illustrated. Signals from the cosine demodulator appearing on conductor 334 are transmitted through resistor 344 to the input of an operational amplifier 346. Transistor 348 having a grounded base is connected in the feedback loop of operational amplifier 346. The voltage-current characteristics of the transistor 348 are essentially logarithmic in character, and the use of the transistor in the feedback loop causes the first stage of the log convertor to be a logarithmic amplifier, thereby causing the output voltage of the logarithmic amplifier to be proportional to the antilogarithm of the input voltage on conductor 334. The variable resistor 340 is connected to a power supply at terminals 350, and a resistor 354 connects tap 352 of the variable resistor 340 to the input of the logarithmic amplifier stage. By varying the position of tap 352, a predetermined bias is summed with the input signal from conductor 334. This predetermined bias is essential in causing a high degree of linear correspondence between the output provided and the distance measured over a portion of the effective measurement range. The foregoing described use of a transistor in the feedback path of an operational amplifier to cause logarithmic amplification characteristics is well known in the art; however, the addition of a pre-determined bias to the essentially logarithmic input signal helps provide a high degree of linear correspondence between the distance measured and the output provided.

The second stage of the log convertor comprises an operational amplifier 356 and forms a voltage follower stage. This stage buffers the output from the logarithmic amplifier stage, and provides an output precisely following the output of the logarithmic amplifier stage regardless of the impedance to which the operational amplifier 356 is connected.

Operational amplifier 358 is used as a summing amplifier for amplifying the output signal from operational amplifier 356. Variable resistance 342 connected to a power supply at terminals 360 supplies a variable bias by means of tap 362 connected to resistor 363 to the input of the operational amplifier 358. This variable bias is added to the output from amplifier 356 and causes the output to be adjustable to a zero reading. By adjusting the variable resistor 342, the zero output at the terminals 338 is provided at the selected zero or reference distance from which the extent of the movement of the object will be measured. Variable resistor 364 in the feedback path of the amplifier 358 provides a means for adjusting the gain of the amplifier 358. By gain adjustment of variable resistor 364, an output voltage magnitude bearing a direct correspondence to the distance measured from the zero reference point may be obtained. A gain adjustment knob or controller can be provided, for example, on base 22 (FIG. 2). Operational amplifier 366 is an inverting amplifier having low-pass filtering. This filtering attenuates any ripple which may be present as a result of the high frequency signal at any of the preceding stages. The inversion characteristic of the amplifier 366 is necessary so as to provide an increasing voltage input at terminals 338 with an increasing distance measured.

The operation of an inductive transducer of the type illustrated at numeral 322 can be described as follows. An inductive transducer can have impedance characteristics that vary primarily in accordance with the type of object whose displacement distance is sensed. For example, if an object of magnetic material is introduced into proximity with the inductive transducer, the inductive reactance of the transducer is normally increased. If the object is non-magnetic material, the inductive reactance is normally decreased. The higher permeability of the magnetic material adds to the self-inductance of the inductive transducer to increase the inductive reactance, but eddy currents induced in the surface of non-magnetic materials cause a counteracting magnetic field to decrease the inductive reactance. However, eddy currents are also sometimes induced in the surface of magnetic materials causing an eddy current effect that tends to counteract the effect of increased self-inductance of the transducer. Thus, with magnetic materials it can be stated in a general way that the inductive reactance of the transducer will be increased by the introduction of magnetic materials near the transducer.

Figures 14, 15:
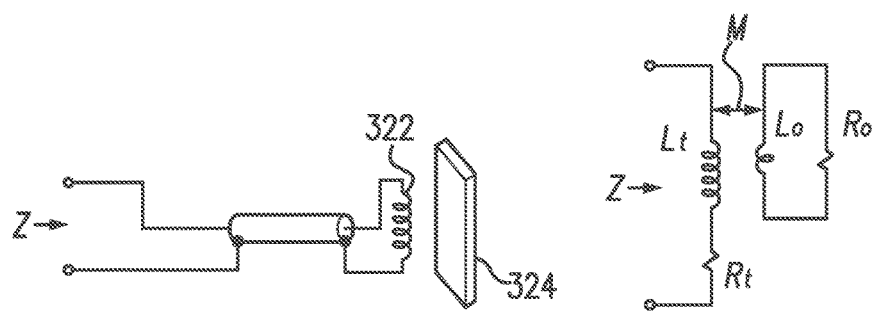
FIG. 14 is perspective view of an inductive transducer shown in FIG. 12, and an object, the distance to which is to be measured.
FIG. 15 is an alternative circuit diagram, relative to the circuit diagram shown in FIG. 14.

FIG. 14 is perspective view of the inductive transducer shown in FIG. 12 and an object to be measured. FIG. 15 is an equivalent circuit diagram of the view shown in FIG. 14. A useful concept in analyzing the performance and operation of an inductive transducer is to consider its analogy to an air core transformer. FIG. 14 illustrates a conventional inductive transducer 322 illustrated as being used to measure the displacement distance between itself and a metal object 324. FIG. 15 illustrates an analogous air core transformer circuit of FIG. 14. The impedance Z described mathematically in terms of the circuit of FIG. 15 provides a relationship of the physical effect of movement of object 324 in relation to the impedance of inductive transducer 322. The equivalent inductance of the object 324 is shown as $L_o$ and its resistance is indicated as $R_o$. The self-inductance of the transducer 322 is illustrated as $L_t$ while its inherent resistance is $R_t$. Although the equivalent inductance and resistance in the induced current path of the object cannot be measured, their presence is reflected in the resistive and reactive components of the impedance of the primary winding of the air core transformer. The mutual inductance M between the primary and secondary winding inductances $L_t$, $L_o$, respectively, is related to the physical displacement between the transducer 322 and the object 324. The derivation of the desired relationship is readily obtainable by well-known methods of circuit and network analysis. Employing this relationship makes it possible to obtain an indication of the relative displacement between the transducer and the object merely by measuring the impedance of the primary winding.

Other circuitry can be used as would be apparent to those of skill in the art given the present teachings, including logarithmic amplifiers of different varieties. Exemplary circuitry that can also or instead be used includes that described in the publication for the Texas Instruments device LOG101, entitled "Precision LOGARITHMIC AND LOG RATIO AMPLIFIER," SBOS242B—May 2002—Revised June 2004, Burr-Brown Products from Texas Instruments, Texas Instruments Incorporated, Dallas, Tex. Moreover, suitable circuitry is also described in the publication for the maxim integrated device MAX2406 entitled "MAX4206 Precision Transimpedance Logarithmic Amplifier with Over 5 Decades of Dynamic Range," 19-3071; Rev. 2; 5/15 available from maxim integrated, San Jose, Calif. Both of these publications are incorporated herein in their entireties by reference.

Figure 16:
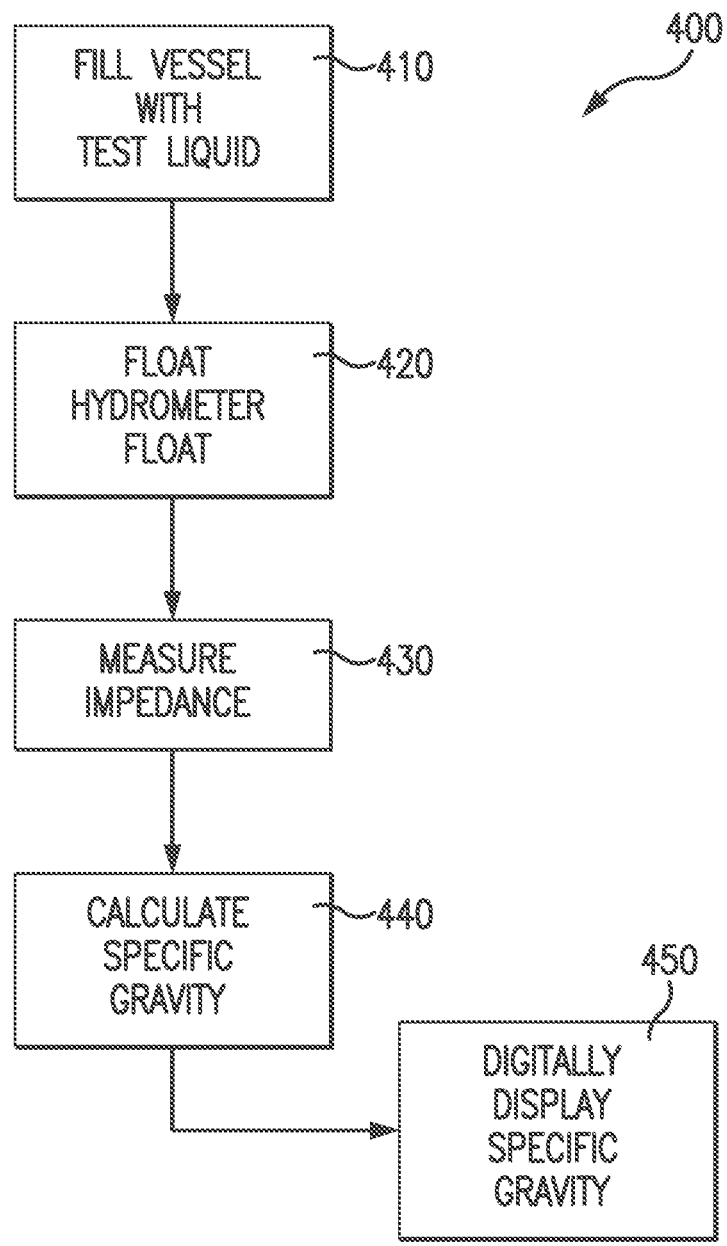
FIG. 16 is a flow diagram depicting a specific gravity measurement method in accordance with the present invention.

FIG. 16 is a flow diagram depicting a specific gravity measurement method 400 in accordance with the present invention. Specific gravity measurement method 400 includes a measurement method first step 410 comprising filling a displacement vessel of a digital hydrometer with a test liquid. Measurement method second step 420 comprises floating a hydrometer float having a metallic object incorporated therein or therewith, in the test liquid. Measurement method third step 430 comprises measuring a change in impedance resulting from the metallic object of the hydrometer float affecting impedance generated by the inductive sensor. Measurement method fourth step 440 comprises calculating a specific gravity (value) using the change in impedance measured in measurement method third step 430. Measurement method fifth step 450 comprises digitally displaying the specific gravity calculated in measurement method fourth step 440.

Figure 17:
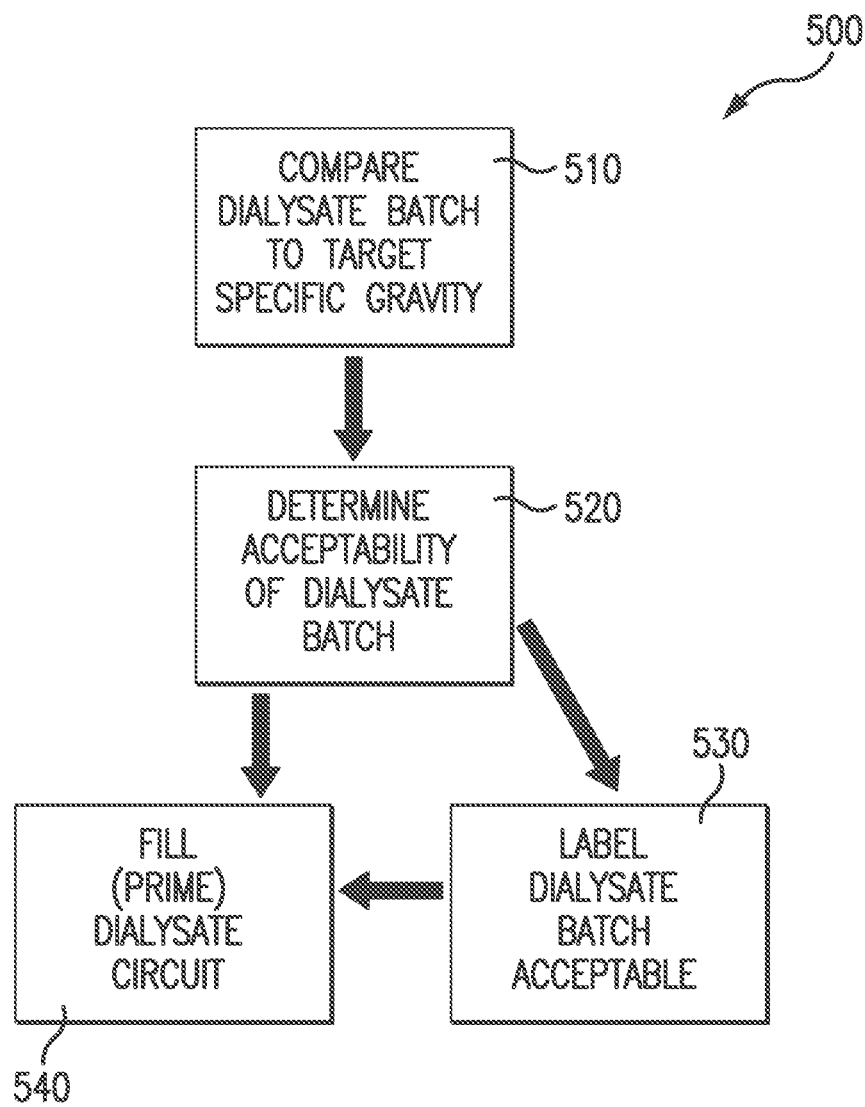
FIG. 17 is a flow diagram depicting a dialysate, specific gravity testing method in accordance with the present invention.

FIG. 17 is a flow diagram depicting a dialysate, specific gravity testing method 500 in accordance with the present invention. Dialysate, specific gravity testing method 500 includes a testing method first step 510 comprising comparing a specific gravity of an acid concentrate batch to a target specific gravity value or range. Testing method second step 520 comprises determining the acceptability of the acid concentrate batch if its specific gravity is sufficiently close to the target, specific gravity value or within a target, specific gravity range. Testing method third step 530 comprises labeling the acid concentrate batch as acceptable if it is determined to be acceptable in testing method second step 520. Testing method fourth step 540 comprises infusing a dialysate circuit of a dialysis or ultrafiltration machine with the acid concentrate batch if the batch is determined to be acceptable. Testing method fourth step 540 can be performed with or without labeling the acid concentrate batch as acceptable as shown in step 530.

The present invention includes the following aspects/embodiments/features in any order and/or in any combination:

1. The present invention relates to a digital hydrometer comprising:
   a base having a top surface;
   a displacement vessel mounted in or on the base and extending upwardly from the top surface;
   an inductive distance sensor mounted in or on the base and comprising an inductor that provides an impedance that varies in relation to a proximity of a metal object in the displacement vessel;
   an output circuit in electrical communication with the inductive distance sensor and comprising a digital display device configured to display a digital value that is commensurate with a change in impedance attributable to the proximity of a metallic object to the inductor; and
   a hydrometer float having a top end and a bottom end, that is sized and configured to float in a displacement fluid in the displacement vessel, and that comprises a metallic object that changes the impedance provided by the inductor, the metallic object being positioned at a fixed distance from the bottom end and the change in impedance varying in relation to the proximity of the metallic object to the inductor,
   wherein the output circuit is configured to generate a signal based on the change of impedance caused by the metallic object, and to convert the signal into a digital value to be displayed by the digital display device.

2. The digital hydrometer of any preceding or following embodiment/feature/aspect, wherein the inductor comprises a single coil inductor.

3. The digital hydrometer of any preceding or following embodiment/feature/aspect, further comprising an induction circuit that comprises a high frequency signal source and an electronic bridge connected to the high frequency signal source, the electronic bridge comprising a plurality of branches including a first branch that comprises the inductor.

4. The digital hydrometer of any preceding or following embodiment/feature/aspect, wherein the high frequency signal source comprises an oscillator, the inductor comprises a single coil inductor, and the plurality of branches further comprises a second branch, a third branch, and a fourth branch each of which provides a fixed, known impedance.

5. The digital hydrometer of any preceding or following embodiment/feature/aspect, wherein the base comprises a base housing and the output circuit is contained in and on the base housing.

6. The digital hydrometer of any preceding or following embodiment/feature/aspect, wherein the digital display device is mounted on the base housing.

7. The digital hydrometer of any preceding or following embodiment/feature/aspect, wherein the digital display comprises a seven-digit display, an LCD display, an LED display, a numerical display, a threshold display, a bulb, an LED, a color indicator, or a combination thereof.

8. The digital hydrometer of any preceding or following embodiment/feature/aspect, wherein the base further comprises a data outlet in electrical communication with the output circuit and configured to transmit output data, via a wired or a wireless connection, to an external device.

9. A system comprising the digital hydrometer of any preceding or following embodiment/feature/aspect and an external device configured to receive output data from the digital hydrometer, wherein the external device comprises a computer, a network, a handheld device, a mixer, a dialysate concentrate mixing device, a dialysis machine, or a combination thereof.

10. The digital hydrometer of any preceding or following embodiment/feature/aspect, further comprising a calibration circuit in electrical communication with and configured to calibrate the inductive distance sensor.

11. The digital hydrometer of any preceding or following embodiment/feature/aspect, further comprising a processor circuit in digital communication with the inductive distance sensor and configured to calculate a specific gravity of a displacement fluid in the displacement vessel based on a signal generated by the output circuit, and to digitally display the calculated specific gravity.

12. The digital hydrometer of any preceding or following embodiment/feature/aspect, further comprising a memory circuit in digital communication with the processor circuit and configured to store the calculated specific gravity.

13. The digital hydrometer of any preceding or following embodiment/feature/aspect, wherein the hydrometer float comprises a hollow shaft containing a gas and the metallic object is fixed at the bottom end.

14. The digital hydrometer of any preceding or following embodiment/feature/aspect, wherein the metallic object is housed within the hollow shaft at the bottom end.

15. The digital hydrometer of any preceding or following embodiment/feature/aspect, wherein the metallic object comprises iron, copper, aluminum, silver, gold, platinum, nickel, palladium, molybdenum, tungsten, iridium, titanium, zinc, tin, cobalt, mercury, or a combination thereof.

16. The digital hydrometer of any preceding or following embodiment/feature/aspect, wherein the metallic object comprises a sheet, a foil, a wire, a wound wire, a coil, a solenoid, a mesh, particles, a spheroid, a nodule, a rod, a tube, a cylinder, a cone, a torus, a hollow body, a solid body, a coating, a dispersion, a suspension, or a combination thereof.

17. The digital hydrometer of any preceding or following embodiment/feature/aspect, wherein the metallic object comprises a magnetic material.

18. The digital hydrometer of any preceding or following embodiment/feature/aspect, wherein the hydrometer float comprises a graduated ruler having indicia corresponding to specific gravity values.

19. The digital hydrometer of any preceding or following embodiment/feature/aspect, wherein the hydrometer float is graduated and comprises an induction adapter module comprising the metallic object and attached at the bottom end.

20. The digital hydrometer of any preceding or following embodiment/feature/aspect, wherein the induction adapter module is attached to the analog hydrometer by suction, adhesive, a friction fit, a snap-fit, a screw fit, a clamp fit, a luer fit, or a combination thereof.

21. The digital hydrometer of any preceding or following embodiment/feature/aspect, wherein the displacement vessel has a hollow cylindrical shape, an interior, an interior diameter, a top end, and an opening to the interior at the top end, and the hydrometer float comprises a maximum outer diameter that is slightly smaller than the interior diameter of the displacement vessel.

22. The digital hydrometer of any preceding or following embodiment/feature/aspect, wherein the maximum outer diameter is smaller than the interior diameter by a distance of from one millimeter to ten millimeters.

23. The digital hydrometer of any preceding or following embodiment/feature/aspect, wherein the hydrometer float has a length, and a ratio of the length to the maximum outer diameter is from about 2:1 to about 20:1.

24. The digital hydrometer of any preceding or following embodiment/feature/aspect, further comprising a displacement fluid contained in the displacement vessel, wherein the displacement fluid comprises a dialysate or a dialysate concentrate.

25. A method of calculating a specific gravity of a test liquid, the method comprising:
    placing a first measured amount of the test liquid in a displacement vessel, the top of the liquid defining a liquid surface;
    floating a hydrometer float in the test liquid in the displacement vessel, the hydrometer float comprising a metallic object configured to change the impedance produced by an inductor (of an inductive distance sensor) by an amount that varies based on the proximity of the metallic object to the inductor, wherein the hydrometer float comprises a top end and a bottom end and is of a buoyancy that causes the top end to extend above the liquid surface and the bottom end to be submerged in the test liquid below the liquid surface;
    measuring an impedance caused by the proximity of the metallic object to the inductor; and
    calculating the specific gravity of the liquid by converting the impedance to a corresponding specific gravity value.

26. The method of any preceding or following embodiment/feature/aspect, further comprising measuring a base impedance before floating the hydrometer float, and wherein the conversion is performed via a difference in impedance between the metal object impedance and the base impedance.

27. The method of any preceding or following embodiment/feature/aspect, wherein the calculating comprises converting the measured impedance to a distance value, representing a linear displacement between the metallic object and the inductor, and then converting the distance value to the corresponding specific gravity value.

28. The method of any preceding or following embodiment/feature/aspect, wherein the method further comprises:
    emptying the test liquid from the displacement vessel;
    placing a second measured amount of a calibration standard liquid having a known specific gravity, in the displacement vessel;
    floating the hydrometer float in the calibration standard liquid in the displacement vessel; and
    measuring the impedance caused by the proximity of the metallic object to the inductor while the hydrometer float is floating in the calibration standard liquid in the displacement vessel, wherein the second measured amount is the same as the first measured amount and the calculating comprises comparing the impedance measured by floating the hydrometer float in the test liquid in the displacement vessel with the impedance measured by floating the hydrometer float in the calibration standard liquid in the displacement vessel.

29. The method of any preceding or following embodiment/feature/aspect, wherein the method further comprises:
    emptying the displacement vessel of the test liquid;
    placing a second measured amount of a first calibration standard liquid having a known specific gravity, in the displacement vessel;
    floating the hydrometer float in the first calibration standard liquid in the displacement vessel;
    measuring the impedance caused by the proximity of the metallic object to the inductor while the hydrometer float is floating in the first calibration standard liquid in the displacement vessel;

emptying the first calibration standard liquid from the displacement vessel;

placing a third measured amount of a second calibration standard liquid having a known specific gravity, in the displacement vessel;

floating the hydrometer float in the second calibration standard liquid in the displacement vessel;

measuring the impedance caused by the proximity of the metallic object to the inductor while the hydrometer float is floating in the second calibration standard liquid in the displacement vessel, emptying the second calibration standard liquid from the displacement vessel;

placing a fourth measured amount of a third calibration standard liquid having a known specific gravity, in the displacement vessel;

floating the hydrometer float in the third calibration standard liquid in the displacement vessel;

measuring the impedance caused by the proximity of the metallic object to the inductor while the hydrometer float is floating in the third calibration standard liquid in the displacement vessel; and generating a calibration curve based on the impedance measured for the first, second, and third calibration standard liquids, wherein the first, second, third, and fourth measured amounts are substantially the same and the calculating comprises comparing the impedance measured by floating the hydrometer float in the test liquid with calibration curve.

30. The method of any preceding or following embodiment/feature/aspect, wherein the calculating comprises using a pre-determined calibration curve, a standard table, or a formula.

31. The method of any preceding or following embodiment/feature/aspect, wherein the curve, table, or formula is based on or normalized to the metallic object used to measure the impedance in the test liquid.

32. The method of any preceding or following embodiment/feature/aspect, wherein the test liquid comprises a dialysate and the method further comprises:

comparing the specific gravity calculated for the dialysate to a target specific gravity value or to a range of acceptable specific gravities;

determining that the specific gravity of the dialysate is sufficiently close to the target value or in the range; and then filling a dialysis circuit of a dialysis machine with the dialysate.

33. The method of any preceding or following embodiment/feature/aspect, wherein the test liquid comprises a dialysate concentrate batch and the method further comprises:

comparing the specific gravity calculated for the dialysate concentrate batch to a target value or a range of acceptable values;

determining that the specific gravity of the dialysate is sufficiently close to the target value or in the range; and then labeling the dialysate concentrate batch as being acceptable to use.

34. The method of any preceding or following embodiment/feature/aspect, wherein the dialysate concentrate batch comprises an acid concentrate.

35. The method of any preceding or following embodiment/feature/aspect, wherein the placing a first measured amount comprises filling the displacement vessel so that the liquid surface rests at a predetermined demarcation on the displacement vessel.

36. The method of any preceding or following embodiment/feature/aspect, further comprising digitally displaying the calculated specific gravity value.

The present invention can include any combination of these various features or embodiments above and/or below, as set forth in the foregoing sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such specific ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A digital hydrometer comprising:
a base having a top surface;
a displacement vessel mounted in or on the base and extending upwardly from the top surface, having an interior, a top end, and an opening to the interior at the top end;
an inductive distance sensor mounted in or on the base and comprising an inductor that provides an impedance that varies in relation to a proximity of a metal object in the displacement vessel;
an output circuit in electrical communication with the inductive distance sensor and comprising a digital display device configured to display a digital value that is commensurate with a change in impedance attributable to the proximity of a metallic object to the inductor; and
a hydrometer float comprising a stem at a top end and a bulb at a bottom end, the hydrometer float being sized and configured to pass through the opening at the top end of the displacement vessel and float in a displacement fluid in the displacement vessel, the hydrometer float further comprising a metallic object in the bulb that changes the impedance provided by the inductor, the metallic object being positioned at a fixed distance from the bottom end and the change in impedance varying in relation to the proximity of the metallic object to the inductor,
wherein the output circuit is configured to generate a signal based on the change of impedance caused by the metallic object, and to convert the signal into a digital value to be displayed by the digital display device.

2. The digital hydrometer of claim 1, wherein the metallic object comprises a magnetic material.

3. The digital hydrometer of claim 1, wherein the displacement vessel has a hollow cylindrical shape and an interior diameter, and the hydrometer float comprises a maximum outer diameter that is slightly smaller than the interior diameter of the displacement vessel.

4. The digital hydrometer of claim 1, wherein the inductor comprises a single coil inductor.

5. The digital hydrometer of claim 1, further comprising an induction circuit that comprises a high frequency signal source and an electronic bridge connected to the high frequency signal source, the electronic bridge comprising a plurality of branches including a first branch that comprises the inductor.

6. The digital hydrometer of claim 5, wherein the high frequency signal source comprises an oscillator, the inductor comprises a single coil inductor, and the plurality of branches further comprises a second branch, a third branch, and a fourth branch each of which provides a fixed, known impedance.

7. The digital hydrometer of claim 1, further comprising a processor circuit in digital communication with the inductive distance sensor and configured to calculate a specific gravity of a displacement fluid in the displacement vessel based on the signal generated by the output circuit, and to provide the calculated specific gravity as the digital value to be displayed by the output circuit on the digital display device, and a memory circuit in digital communication with the processor circuit and configured to store the calculated specific gravity.

8. A digital hydrometer comprising:
a base having a top surface;
a displacement vessel mounted in or on the base and extending upwardly from the top surface;
an inductive distance sensor mounted in or on the base and comprising an inductor that provides an impedance that varies in relation to a proximity of a metal object in the displacement vessel;
an output circuit in electrical communication with the inductive distance sensor and comprising a digital display device configured to display a digital value that is commensurate with a change in impedance attributable to the proximity of a metallic object to the inductor; and
a hydrometer float comprising a stem at a top end and a bulb at a bottom end, the hydrometer float being sized and configured to float in a displacement fluid in the displacement vessel, the hydrometer float further comprising a metallic object in the bulb that changes the impedance provided by the inductor, and the hydrometer float further comprising a hollow shaft containing a gas, wherein the metallic object is positioned at a fixed distance from the bottom end and the change in impedance varies in relation to the proximity of the metallic object to the inductor,
wherein the output circuit is configured to generate a signal based on the change of impedance caused by the metallic object, and to convert the signal into a digital value to be displayed by the digital display device.

9. The digital hydrometer of claim 8, wherein the metallic object comprises a sheet, a foil, a wire, a wound wire, a coil, a solenoid, a mesh, particles, a spheroid, a nodule, a rod, a tube, a cylinder, a cone, a torus, a hollow body, a solid body, a coating, a dispersion, a suspension, or a combination thereof.

10. A digital hydrometer comprising:
a base having a top surface;
a displacement vessel mounted in or on the base and extending upwardly from the top surface;
an inductive distance sensor mounted in or on the base and comprising an inductor that provides an impedance that varies in relation to a proximity of a metal object in the displacement vessel;
an output circuit in electrical communication with the inductive distance sensor and comprising a digital display device configured to display a digital value that is commensurate with a change in impedance attributable to the proximity of a metallic object to the inductor; and
a hydrometer float having a top end and a bottom end, that is sized and configured to float in a displacement fluid in the displacement vessel, and that comprises a metallic object that changes the impedance provided by the inductor, the metallic object being positioned at a fixed distance from the bottom end and the change in impedance varying in relation to the proximity of the metallic object to the inductor,
wherein the output circuit is configured to generate a signal based on the change of impedance caused by the metallic object, and to convert the signal into a digital value to be displayed by the digital display device, and the hydrometer float is graduated and comprises an induction adapter module comprising the metallic object and attached at the bottom end.

11. The digital hydrometer of claim 10, wherein the induction adapter module is attached to the analog hydrometer by suction, adhesive, a friction fit, a snap-fit, a screw fit, a clamp fit, a luer fit, or a combination thereof.

* * * * *